United States Patent [19]

Savic

[11] Patent Number: 5,623,421

[45] Date of Patent: Apr. 22, 1997

[54] MONITORING PRESSURIZED VESSELS FOR LEAKS, RUPTURES OR HARD HITS

[75] Inventor: Michael Savic, Ballston Lake, N.Y.

[73] Assignee: Rensselaer Polytechnic Institute, Troy, N.Y.

[21] Appl. No.: 552,542

[22] Filed: Nov. 3, 1995

[51] Int. Cl.$^6$ .................................................. G01M 3/24
[52] U.S. Cl. ........................ 364/510; 364/509; 73/40.5 A
[58] Field of Search ............................ 367/117; 376/252; 73/52, 584, 587, 659, 40, 40.5 R, 40.5 A, 49.2, 570, 592, 579, 49.3; 340/603, 605; 364/506, 509, 510

[56] References Cited

U.S. PATENT DOCUMENTS

| | | | |
|---|---|---|---|
| 4,201,092 | 5/1980 | Dau | 73/587 |
| 4,455,863 | 6/1984 | Huebler et al. | 73/40.5 A |
| 4,543,817 | 10/1985 | Sugiyama | 73/405 A |
| 4,960,079 | 10/1990 | Marziale et al. | 73/40.5 A |
| 5,341,670 | 8/1994 | Brook et al. | 73/40.5 A |
| 5,416,724 | 5/1995 | Savic | 364/509 |

*Primary Examiner*—Emanuel T. Voeltz
*Assistant Examiner*—Craig Steven Miller
*Attorney, Agent, or Firm*—Notaro & Michalos P.C.

[57] ABSTRACT

A device monitors a pressurized vessel to detect small leaks, ruptures and hard hits on the vessel. Transducers are attached to the vessel and transmit acoustic signals which are processed to extract frequency spectra which contain dominant resonant frequency peaks, if the vessel contains a small leak. If multiple frequency component of the spectra shift to a lower frequency suddenly and stay at the lower frequency, this indicated the presence of a larger leak or rupture. A hard hit on the vessel, for example by machinery, is detected by a shift in the transient response of harmonics in the acoustic signal.

15 Claims, 8 Drawing Sheets

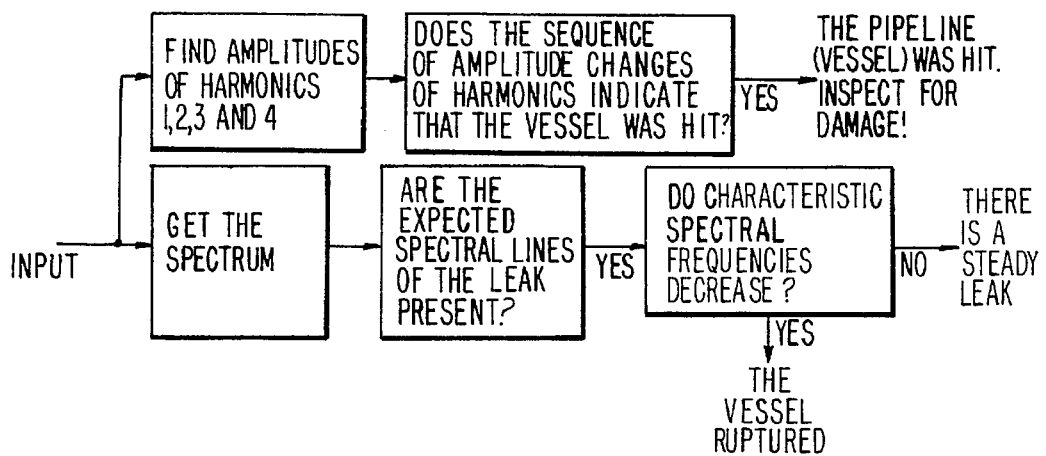
FIG. 7
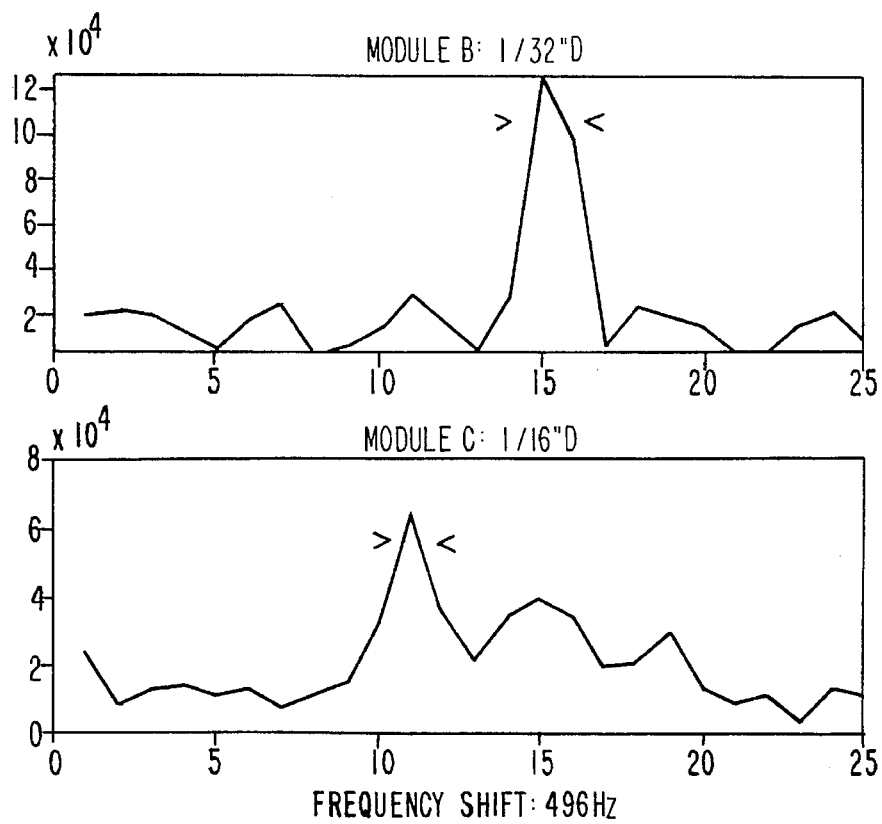
FIG.12A
FIG.12B

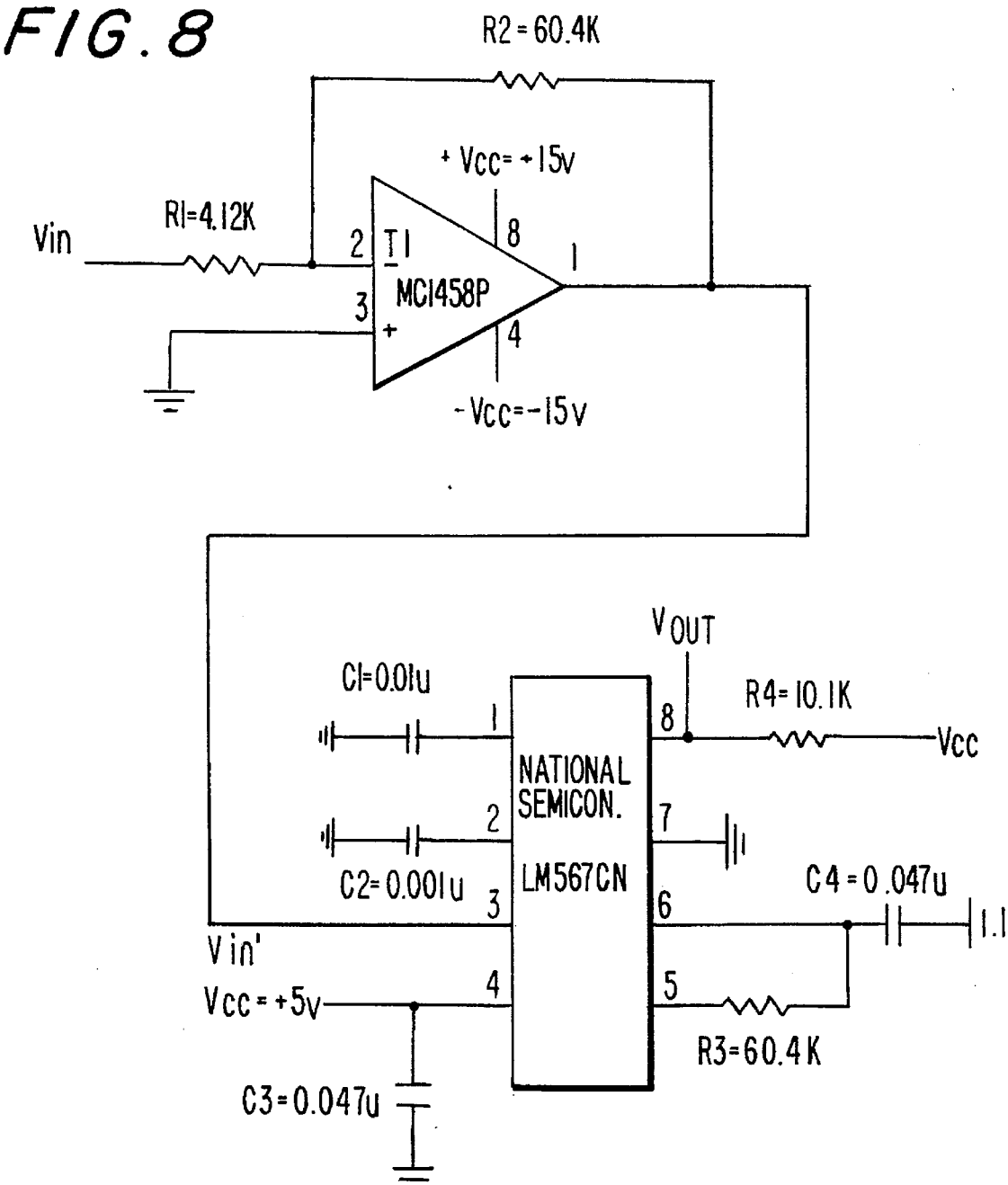

MONITORING PRESSURIZED VESSELS FOR LEAKS, RUPTURES OR HARD HITS

FIELD AND BACKGROUND OF THE INVENTION

The present invention is related in general to the acoustic monitoring of pipelines and vessels which carry pressurized gas or liquid, and in particular to a new and useful method and apparatus of monitoring pressurized vessels for small leaks, explosions or hard hits.

U.S. Pat. No. 5,416,724, which is incorporated here by reference, was issued May 16, 1995 to the inventor of the present application. That patent disclosed a technique for detecting leaks in pressurized pipelines or vessels, using an acoustic sensor and in conjunction with a specific technique of analysis for analyzing the signals from the acoustic sensor to identify the presence of a leak.

Fast, reliable detection of large or small leaks of gaseous and liquid materials from storage and pipeline facilities is an important problem. If the material is explosive, even small holes in high pressure gas pipelines can quickly result in the formation of dangerous, large gas clouds. also if an underground or above ground vessel is struck by a hard object or a power tool, it might be damaged. In a situation like this it is necessary to determine the location of the impact and send a crew to inspect the vessel for possible damage.

Some definitions and assumptions used in this disclosure:

1. In this disclosure the word "vessel" is used to describe a container filled with a gas or liquid under high or low pressure, including containers and pipelines.

2. It is presumed that the vessel may have any shape, such as the shape of a barrel, the shape of a pipeline or other shape.

3. The term "rupture" is used to describe a sudden breach or explosion of the wall of a vessel under pressure, resulting in a large leak.

4. The vessel may be located above ground, underground or submerged in a liquid.

5. Concerning an "acoustic signal", all vessels under pressure have two important characteristics. These characteristics are a) the mechanical resonance of the vessel, and b) the propagation of mechanical waves through the vessel.

a) If a vessel is mechanically excited such as if it is struck by a hard object, the vessel will oscillate (resonate) for a while at it's mechanical resonant frequency. The resonant characteristic includes the amplitude, frequency and the damping factor and it is determined by the dimensions and by the material of which the vessel is made.

If at least one dimension of the vessel is large, it takes time for a sound wave to propagate from one point of the vessel to another, and propagation characteristics of the sound through the vessel must be considered. Since vessels come in many different shapes, a model used in this disclosure will contain both the resonant and the propagation characteristics, and this model will be the pipeline. In other words in this disclosure the pipeline is used to be a representative of all vessels.

Some existing continuous leak detection systems rely on methods such as volume balance comparison [1] while others rely on detection of the leaking fluid [2]. These systems, however, can only detect relatively large leaks and may allow a potentially dangerous situation to develop quickly without detection [3].

[1] W. C. Thompson and K. D. Skogman. "The Application of Real Time Flow Modeling to Pipeline Leak Detection" in K. Chickering, editor, Pipeline Engineering Symposium, pp. 39–45. the American Society of Mechanical Engineers, 1983.
[2] C. Sandbert et al. "The Application of a Continuous Leak Detection System to Pipelines and Associated Equipment," IEEE Transactions on Industry Applications, pp. 906–909, September, October 1989.
[3] S. Olafson, "An Alarm in Tulsa, Then Time Ran Out in Brenham," The Houston Post, pg. A1, nday, Apr. 12, 1992.

SUMMARY OF THE INVENTION

The present invention is a new device and method for continuous monitoring of vessels. The device can detect leaks, ruptures and also when the vessel is struck by a hard object. In addition the device can determine the location of the suspected hazard and alert the responsible person who will dispatch a crew to inspect the vessel for possible damage.

The usefulness of the present invention has been established and verified using models, simulated leaks and actual tests on actual above ground and below ground pipelines that are representative of all vessels that may be tested according to the present invention.

According to the present invention, small leaks in a vessel can be detected by determining a dominant resonant frequency for the vessel, using either experimental or analytical techniques. Frequency spectra for the acoustic signals are than detected at various locations along the vessel. If peaks exist in the spectra, at the dominant resonant frequency or at one or more multiples of the dominant resonant frequency, this has been found to indicate the existence of a small leak in the vessel.

A rupture or a sudden breach in the vessel can be detected, according to the present invention, by observing a sudden shift of the frequency spectra to lower frequencies and the maintenance of the spectra at lower frequencies.

Further, the invention includes a device and method for detecting if and when the vessel is struck by hard objects such as machinery. Such an occurrence is signaled by a transient response of the harmonic peaks in the frequency spectra.

Accordingly, one object of the present invention is to provide a device for monitoring a pressurized vessel for an occurrence of small leaks or ruptures or hard hits, comprising a plurality of acoustic transducers at spaced sensor locations on the vessel, each responsive to sounds from the vessel at each sensor location, to generate acoustic signals from each sensor location and a central processor connected to each of said transducers and including spectra means for repeatedly recording a frequency spectrum of the acoustic signal from each transducer, the central processor including program means containing a dominant resonant frequency for the vessel and analysis means for detecting peaks in each spectra at the dominant frequency, the presence of peaks indication the existence of a small leak in the vessel.

A further object of the present invention is to provide such a device wherein a rupture is detected in the vessel by detecting a sudden shift of the multiple frequency components in the spectra, to a lower frequency, and the maintenance of those components at the lower frequency.

A still further object of the invention is to provide a device for detecting a hard hit to the vessel which includes detecting the transient response of first, and the sequence of peaks of these components in the time domain second and third harmonics in the spectra which indicates the occurrence of a hard hit to the vessel.

A further object of the present invention is to provide a device which is capable of determining the location of the small leak, rupture and/or hard hit, by utilizing a differential attenuation of the first and second harmonics of the spectra, or by utilizing the transmission line characteristics of the acoustic signals.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 7 is a diagram illustrating hardware and steps of a device of the present invention which is capable of detecting small leaks, large ruptures and hard hits on a vessel;

FIG. 8 is a schematic diagram of a phase locked loop based leak detector of the present invention;

FIGS. 12A and 12B are two graphs plotting amplitude against frequency of spectra for a relatively small and a relatively large leak and illustrating the shift in frequency components of the spectra to a lower frequency range indicative of a large rupture;

DESCRIPTION OF THE PREFERRED EMBODIMENTS

Figure 1:
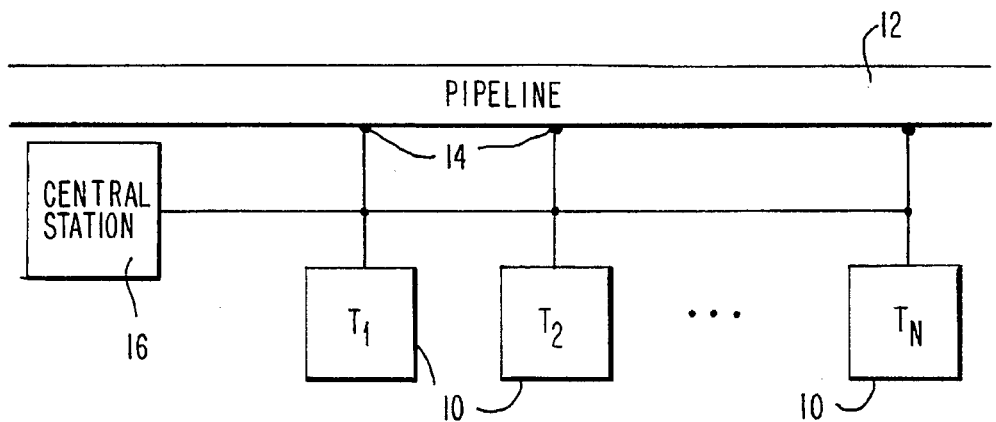
FIG. 1 is a schematic representation of a device according to the present invention for monitoring a vessel, in particular a pipeline in the embodiment disclosed.

The device of the present invention comprises remote signal collection and analysis units 10 in FIG. 1 placed at predetermined distances from each other along the vessel which is assumed to be a pipeline 12 in this disclosure. The sound of a leak signal received at the remote units is picked up by piezoelectric RGT or other transducers 14 attached to the wall of the pipeline and converted into an electric signal. This signal has a complex frequency spectrum that is produced by poles and zeros of the source of the sound, as well as by the poles and zeros of the section of the pipeline between the source of the sound and the location of the transducer, which also vibrate.

If the pipeline is struck by a hard object, if a leak develops, or if a rupture occurs, an acoustic signal will be generated. that signal will travel through the pipeline and will be picked up by the adjacent remote units. Each unit is able to recognize if the sound is a steady leak, a rupture or the sound caused by the pipeline being struck by a hard object. Each unit is also able to discriminate suspicious sounds from all other sounds. In addition each unit 10 ($T_1$–$T_N$) communicates to supervisory personnel at a central station 16, the nature and location of the suspected hazard and alerts the personnel in case of an emergency.

In order to make the system economical it is desirable to place along the pipeline 12 as few of these remote units 10 as possible. It is important, therefore, to know the maximum reliable detection distance. This distance is determined utilizing the distributed parameter model of the pipeline.

The present invention was experimentally verified both on high pressure underground, and on low pressure above ground Texaco pipelines. The above ground pipeline pressurized at low pressure was a Texaco pipeline at a Humble cite in Texas with an external diameter of D=6.625 in (16.828 cm). The underground pipeline was a Texaco ethylene pipeline running from a chemical plant in Port Arthur, Tex. to a storage facility in Sour Lake, Tex. This approximately 40 mile long pipeline has an internal diameter of 7 inches and 0.5 inch thick walls. The internal pressure of that pipeline is 1,500 PSI and the pipeline is buried in soil that is usually damp.

As to the source of the sound, gaseous or liquid media under pressure leaking through a small hole undergo turbulent motions. This turbulence produces a Gaussian excitation that tends to cause the pipeline section close to the leak to oscillate at its resonant frequencies. A pipeline has many resonant frequencies that can be found by equations utilizing Bessel Functions, however only dominant resonant frequencies which give the largest amplitudes are important for the invention. These frequencies can be found experimentally or analytically.

Figure 2:
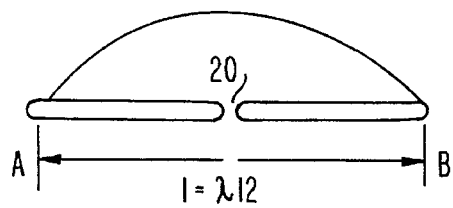
FIG. 2. schematically illustrates a hole in a portion of the wall of a vessel analyzed according to the present invention.

Assume a leak 20 in the Humble, Tex. pipeline, and observing the narrow segment of the pipeline which includes the leak in FIG. 2 and which is perpendicular to the longitudinal axis of the pipeline, consider a circumferential strip of the pipeline, with length l which is the circumference.

The circumference of the pipeline 12 is $$l=D*3.14=52.75 \text{ cm} \tag{1}$$

Figure 9:
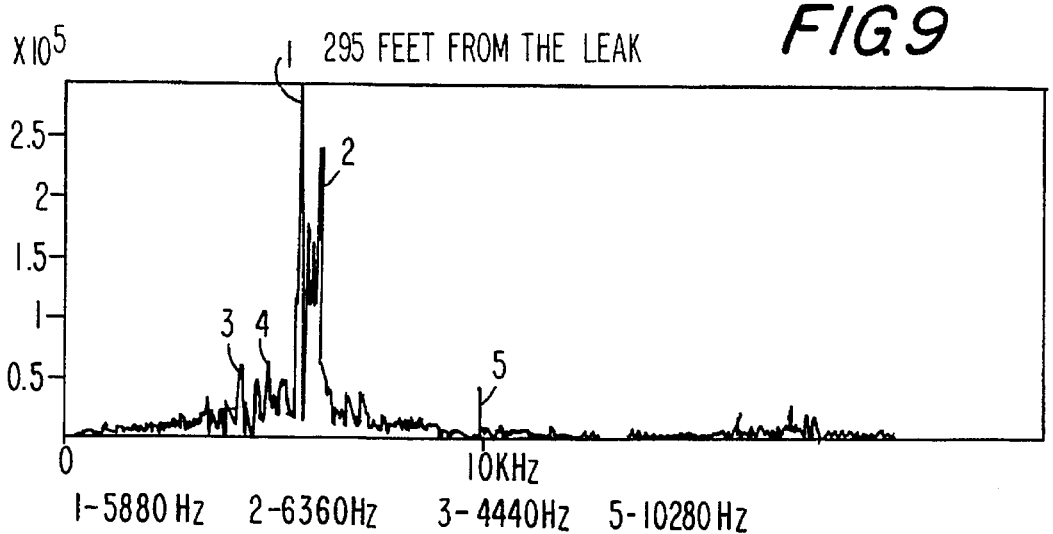
FIG. 9 is a frequency spectrum of an acoustic signal generated according to the present invention, plotting relative amplitude against frequency and illustrating peaks in a dominant resonant frequency and other harmonics and frequency response of an audio signal from a transducer according to the present invention at a first distance from a noise in the vessel indicating the presence of a small leak.
Figure 10:
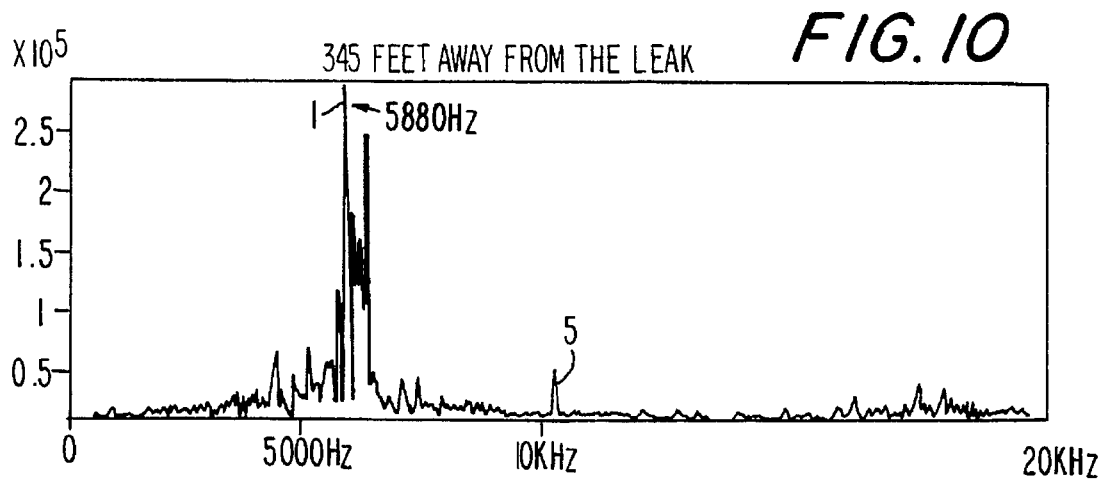
FIG. 10 is a spectrum similar to FIG. 9 at a further distance from the leak.
Figure 11:
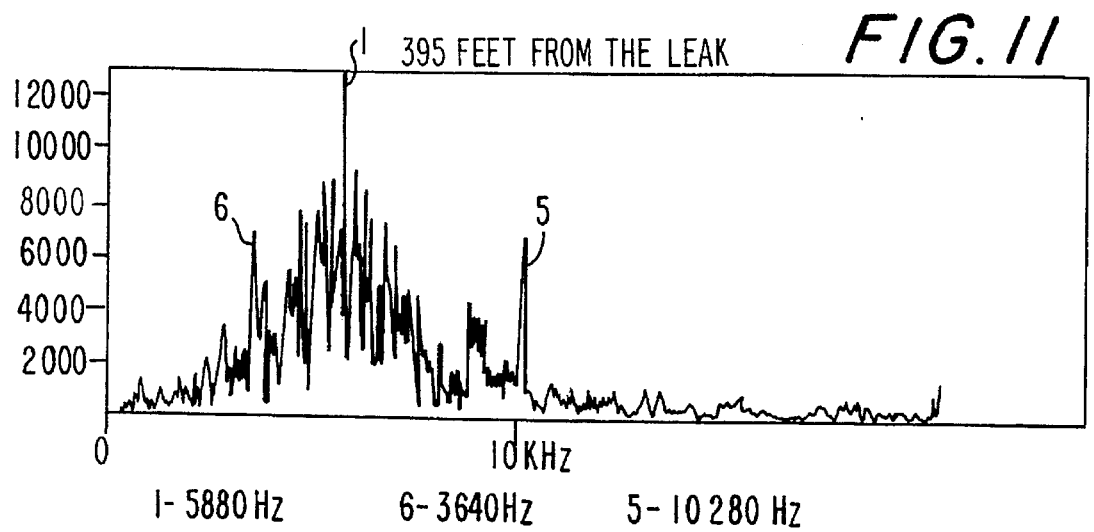
FIG. 11 is a spectrum similar to FIG. 9, taken at a still further distance from the leak.

In order to investigate the propagation along the pipeline of the sound wave created by a small leak, an artificial 1/16" leak was made in the Humble pipeline. Next the frequency responses of the sound received at various distances from the leak were recorded. The recordings showed multiple peaks (resonant frequencies). However, in all recordings, the notable dominant frequency (with the highest peak) was at 5,880 Hz. as shown at 1 in FIG. 9, 10 and 11, and this frequency was independent of the distance between the leak and the place where the sound was recorded. As an example, recordings at distances of 295, 345 and 395 feet from the leak are shown in FIGS. 9–11.

An additional peak at 5, at the frequency of 10,280 Hz. can be seen as well. This peak represents the second harmonic (5,880*2=11,760) of the dominant frequency component, and the slightly incorrect position of that peak is believed to be due to a sampling error.

In order to verify the recorded dominant resonant frequency of the pipeline, this frequency was calculated as well. The corresponding wavelength in steel can be found by using the velocity of propagation of sound in steel c=585,000 m/sec.

$$\lambda = c/f = 585,000/5,880 = 99.49 \text{ cm}$$

The ratio of the circumference to the wavelength is $$l/\lambda = 52.75/99.49 = 0.53 \approx 0.5 \quad (20)$$

i.e.

$$l = 0.5 * \lambda \quad (2)$$

The conclusion is that there is a relationship between the half wavelength of the sound wave $\lambda/2$ and the length of the strip l shown in FIG. 2. In other words the strip acts as a "half-wave acoustic antenna". The maximal displacement of the points along the strip is at the leak 20 and minimal displacement at the points A and B opposite the hole.

Points A and B are actually next to each other since l is the circumference, and at the same location which is opposite the leak, A is on one side of the leak and B on the other. Assuming that due to the boundary conditions the particle displacement at points A and B is zero and that at the leak the particle displacement is maximum, the mechanical resonance will occur when equation (3) is satisfied, for n=1, 3, 5, etc., because only when n is odd will elements of the pipeline that are located to the right of point A and to the left of point B move synchronously in the same direction which is necessary for resonance.

$$l = n * \lambda * /2 \text{ where n is } 1, 3, 5 \quad (3)$$

In this analysis one considers two velocities of propagation. To find the resonant frequency of the pipeline we must use the velocity of sound in steel, however to analyze phenomena related to propagation we must use the velocity in gas. Measurements show that sound propagates simultaneously through the two media. By analyzing the spectra at a large distance from the leak, and by measuring the velocity of propagation through the pipeline the inventor concluded that the longitudinal propagation mode through gas is much less attenuated than the longitudinal mode through the steel wall. Consequently, only the component of sound that propagates through the inside of the pipe is considered. However, for calculations of resonant frequencies of the pipeline, the velocity of propagation through steel given in known tables is used, which is $$c = 585,000 \text{ cm/sec}$$

Using the Humble cite relationship of (3) instead of the approximate relationship of (1), the calculated fundamental resonant frequency for n=1 will occur at $$f = c/\lambda = (585,000)/(2*52.75) = 5545 \text{ Hz} \quad (4)$$

Which is almost identical to the measured value of 5,880 Hz. In addition to the peaks at dominant frequencies, the spectrum contains many other frequency components as well. These frequency components are produced by various modes of oscillations of the cylindrical pipe.

Some of the resonant frequency components are attenuated more than others. The plane wave mode (0, 0) will propagate with a small attenuation, however frequency components at higher modes (m, n) and below the cutoff frequency $f_{c(m,n)}$ will be very much attenuated. Let us determine the cutoff frequencies for some modes for the Texaco pipeline at the Humble cite.

The parameters of the Humble pipeline are:

D'=11.8 cm is the internal diameter of the pipe and c=43,000 cm/sec is the velocity of propagation of sound through gas.

The cutoff frequency for the T(1, 0) mode is $$f_{c(1,0)} = 0.293 * 2 \; c/D' \quad (5)$$

so that $$f_{c(1,0)} = 0.293 * 2 * 43,000/11.8 = 2.135 \text{ KHz} \quad (6)$$

Similarly:
For mode (2.0)

$$f_{c(2,0)} = 0.485 * 2 * 43,000/11.8 = 3.534 \text{ KHz} \quad (7)$$

and for mode (0.1)

$$f_{c(0,1)} = 0.605 * 2 * 43,000/11.8 = 4.409 \text{ KHz} \quad (8)$$

In other words, propagating acoustical waves with frequencies below $f_{c(m,n)}$ will be significantly attenuated while propagating through the pipeline. Consequently the pipeline behaves as a highpass filter with a cutoff frequency $f_{c(m,n)}$. Due to this, low frequency components of the signal are practically eliminated even at short distances from the leak. Consequently frequency components that propagate with small attenuation become predominant and show up as peaks. Some of these components can be easily identified in the spectrum of the received leak signal at any distance from the leak as shown in FIGS. 9, 10 and 11.

Since the frequency of the first harmonic is somewhat lower then the cutoff frequency for propagation of the acoustic wave inside the pipeline, the first harmonic will be considerably attenuated. Consequently the first harmonic is attenuated after a very short time, and the second harmonic becomes dominant. In other words, the second harmonic is not only the strongest harmonic at the source of the leak as shown in FIGS. 9–11, but it will also propagate at large distanced because of small attenuation.

The large leak or rupture can be analyzed analogously to the case of a small leak. If the diameter of the leak increases due to the occurrence of a rupture, the resonant frequency will decrease. This conclusion is also supported by experimental results indicating that the fundamental resonant frequency of the sound is a function of the size of the hole as well. When the size of the hole increases, the fundamental resonant frequency decreases.

It can be seen from the recorded frequency spectra shown on an enlarged frequency scale in FIGS. 12A and 12B, that small holes produce higher frequency (pitch) sounds, and larger holes lower frequency (pitch) sounds. Thus, during the very short transient period, when a rupture occurs, the size of the hole increases rapidly. Due to this, the frequency spectrum of the sound of the leak will decrease during the rupture. At the same time the energy of the sound will increase. The sound of the leak is picked up by the transducer 10 and converted into an electric signal.

The monitoring system of the invention uses the spectra of the leak to determine the character of the leak. A similar technique is successfully used in air to air infrared guided missiles such as in the "Sidewinder". The frequency spectra of the leak signal recorded at the Humble cite at different distances are shown in FIGS. 9–11. these spectra indicate the two characteristic peaks one at 5,880 Hz and the other at 10,280 Hz. The first frequency is the dominant resonant frequency, and the second is the second harmonic. The error of 5.7% between the calculated (5,545 Hz) and measured resonant frequency is in all likelihood due to the difference in the actual velocity of propagation through steel, and the velocity that we took from tables.

These peaks can be detected in many ways. One embodiment of the invention uses Digital Signal Processing (DSP), and another uses a hardware frequency detector—a Phase Locked Loop (PLL).

Figure 3:
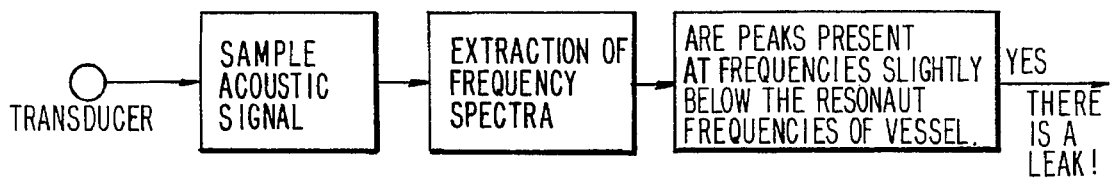
FIG. 3 is a block diagram illustrating the function of the device of the present invention for detecting small leaks.
Figure 4:
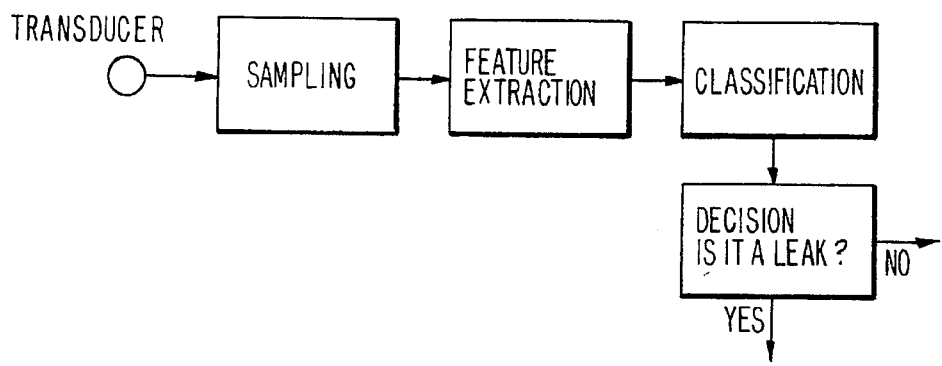
FIG. 4 is a block diagram illustrating the steps of the invention when embodied as a computer.

The steady state leak can be detected by identification of the characteristic peaks in the frequency spectrum. The presence of a leak is indicated if the dominant frequency peaks are present for a long time interval, for instance for 3 minutes. The criterion used in the DSP approach is, sample the received signal and check if there are peaks at frequencies slightly below the mechanical resonant frequency of the vessel (pipeline). See FIG. 3. The invention can be implemented using a TMS 32030 based computer, schematically shown in FIG. 4.

A Phase Locked Loop (PLL) of FIG. 8 can also be used to identify the characteristic frequency peaks of the frequency spectrum. In FIG. 8, the following design features hold:

1. R2/R1=Gain of amplifier.
2. C1≧2*C2.
3. C3>0.01 01uF.
4. Resonant frequency f=1/(1/1*R3*C4).
5. Bandwidth BW=1070 (Vin'/(f*CII))$^{(½)}$.
6. The values shown in FIG. 8 are for f=14.9 KHz The presence of a leak is indicated if the dominant frequency peaks are present for a long time interval, for instance for 3 minutes. When this happens, the output of the PLL goes from low to high.

Figure 5:
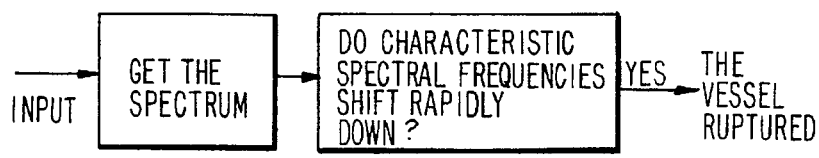
FIG. 5 is a block diagram illustrating the process practiced by the device of the present invention for detecting a rupture.

A rupture is identified as noted above, by detecting a frequency spectrum that quickly shifts towards lower frequencies, and then remains constant. This is detected with two or three phase locked loops tuned to a sequence of frequencies below the natural resonant frequency of the pipe. The rupture is identified when the outputs of these PLL go successively high. Another solution is by identifying the shift using digital signal processing. See FIG. 5.

Figure 13:
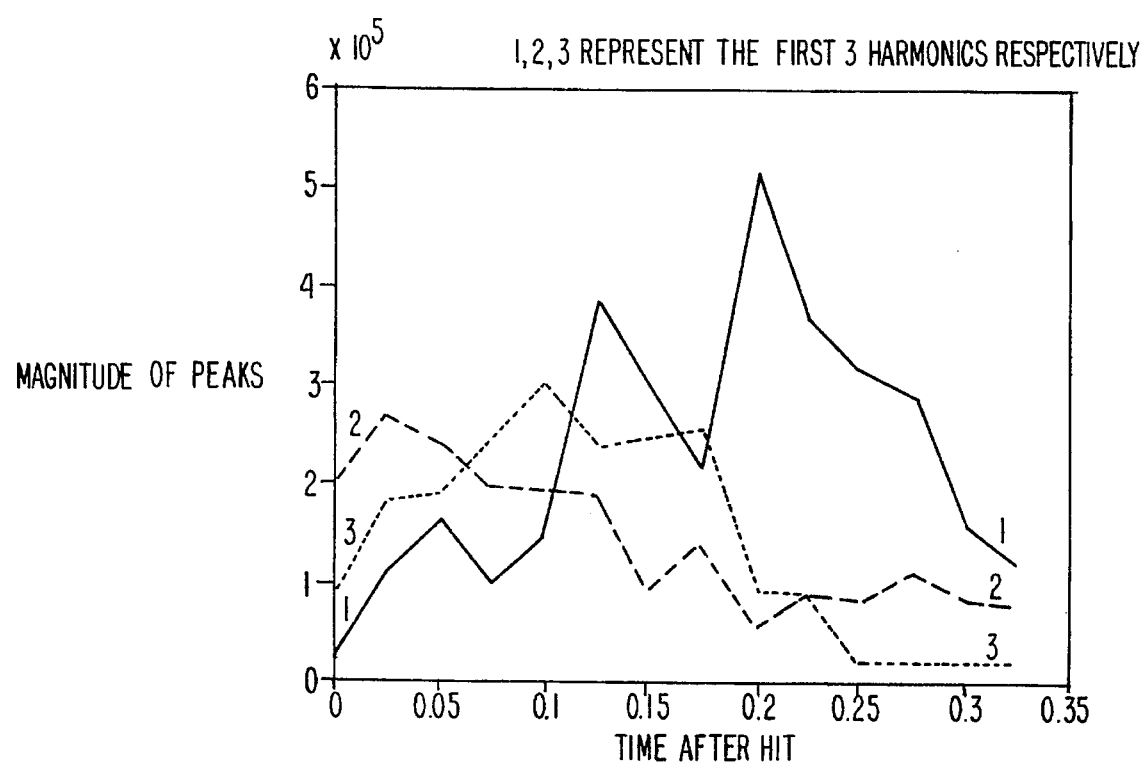
FIG. 13 is a set of curves showing three harmonics of frequency spectra resulting from noise caused by a hard hit on the vessel and illustrating a characteristic delay among the three harmonics which can be used to identify the occurrence of a hard hit.

The event when a pipeline is struck by a tool or by a machine can be determined from the mechanical transient response of the first three harmonics of the natural response of the pipeline. Laboratory experiments show that the mechanical response of the first three harmonics in terms of time, looks like FIG. 13. FIG. 13 shows changes of amplitudes of the first three harmonics in terms of time after the pipe is struck. Bases on the observation of this diagram, it can be concluded that the pipe has been struck. The second harmonic produces the largest amplitude followed by the third and first harmonic. Afterward, during the transient period, the amplitudes of the harmonics change in a characteristic way so that after a long period of time, the first harmonic becomes dominant.

By recording the transient response of the harmonic peaks and by comparing the amplitudes of these harmonics at different time intervals, one can determine with high accuracy, if the pipeline was struck by an object or a machine.

Figure 15:
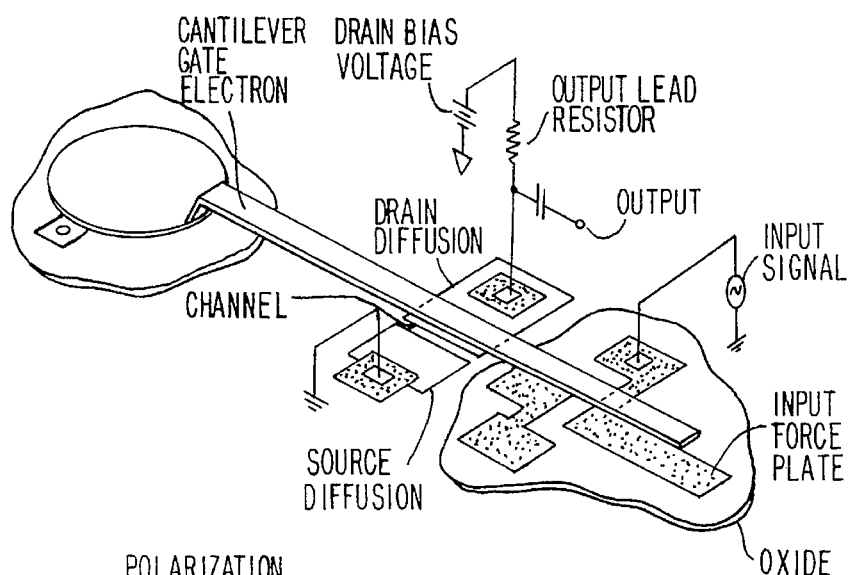
FIG. 15. is a perspective view of the Resonant Gate Transducer (RGT) of the present invention.
Figure 16:
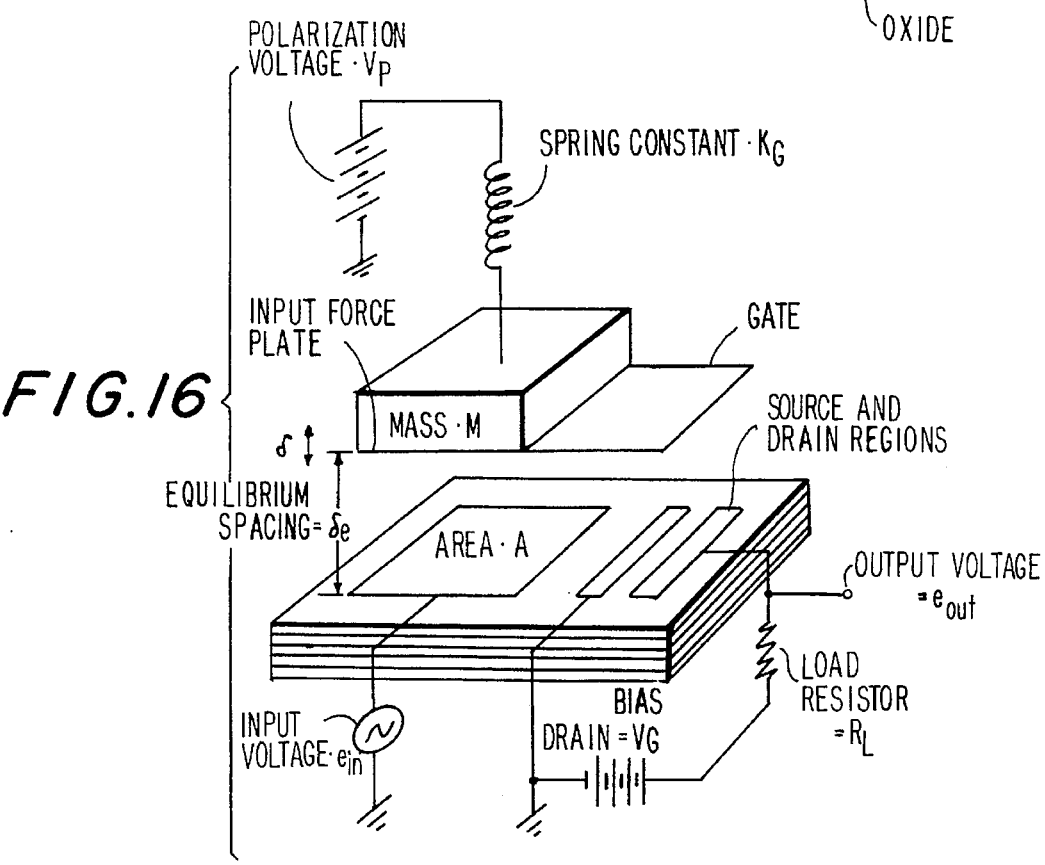
FIG. 16. is an exploded view thereof.
Figure 17:
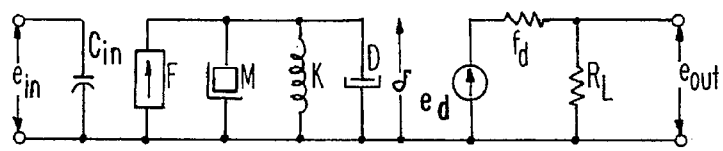
FIG. 17. is an equivalent circuit for the RGT.

Since the frequency at which the resonant peak can be expected to occur can be predicted, it is possible to make a micro-mechanical transducer based on a resonant gate transistor such as the one shown in FIGS. 15–16. The equivalent circuit of the resonant transistor and the frequency response are shown in FIG. 17. The micro-mechanical transducer is small, sensitive, very inexpensive, and it has the right frequency response. This transducer was simulated on a computer.

The Micro-mechanical Transducer is an ideal solution for monitoring leaks in large pipelines, as well as in pipelines for gas distributions in urban areas. The transducer and the preamplifier can be fabricated on the same monolithic integrated circuit (IC) chip.

Based on the theory and experiments of this invention, a gas leak detector of the invention is shown in FIG. 7. The described device can detect steady leaks from cracks as small as 1/32" in diameter in pipelines carrying gas under high pressure. In summary the device detects a leak by the presence of characteristic harmonic peaks in the frequency spectrum.

Figure 6:
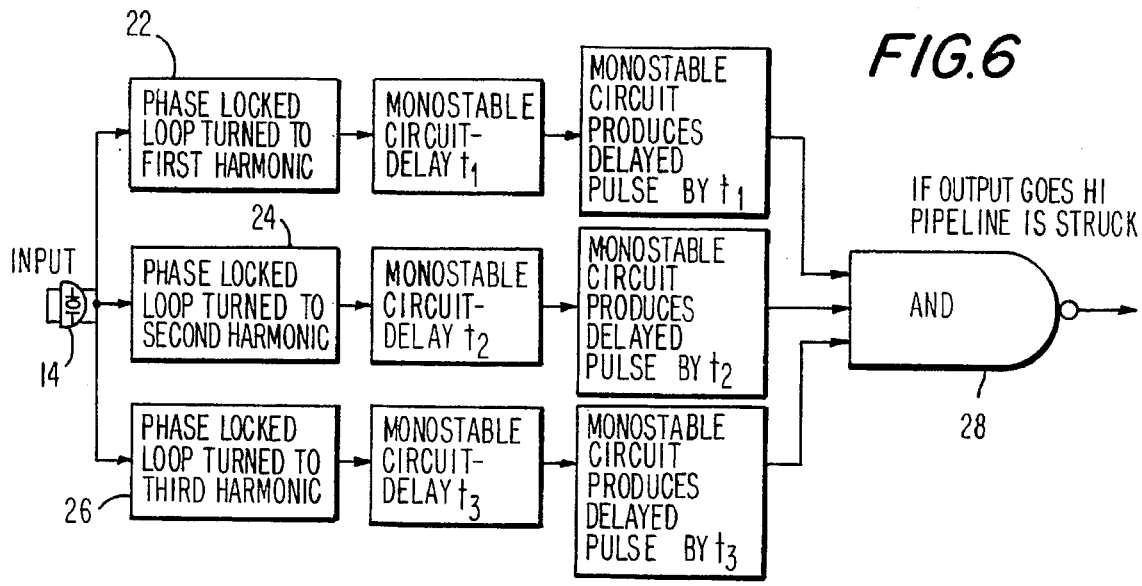
FIG. 6 is a diagram illustrating hardware and steps according to an embodiment of the invention for detecting a hard hit on the vessel.

Based on the research involving a hard hit on the pipeline, the device shown in FIG. 6 was built and tested.

If a pipeline is struck by a hard object, a sound is produced. This sound is picked up by the transducer 14 and brought to three Phase Locked Loops (PLL) 22, 24, 26. Each is tuned to one of the first three harmonics of the mechanical resonance. As mentioned previously, after the pipe is struck, the second harmonic produces the largest amplitude followed by the third and first harmonic.

Figure 14:
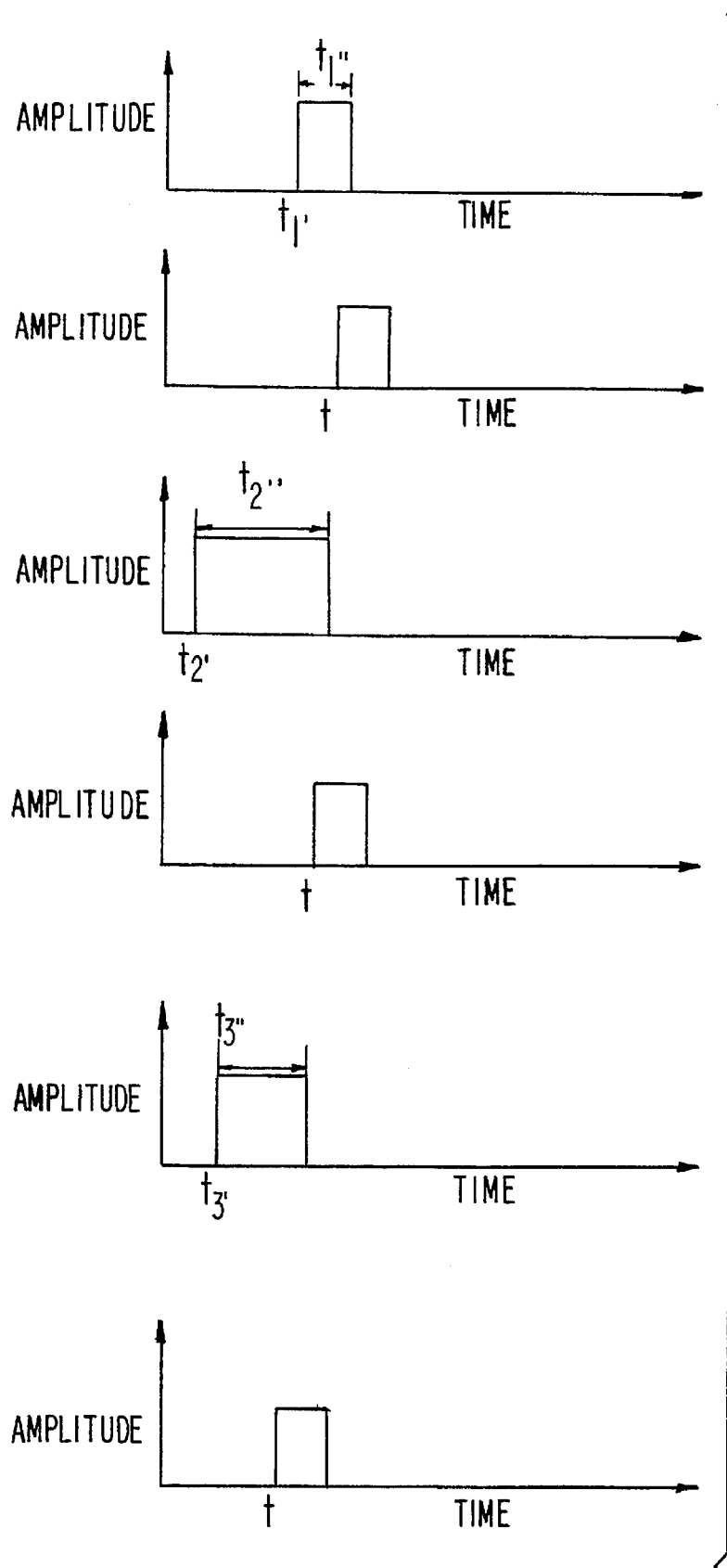
FIG. 14 is a composite timing chart showing delays applied to the three harmonics for detecting occurrence of a hard hit.

Afterward, during the transient period the amplitudes of the harmonics change in a characteristic way so that after a large period of time the first harmonic becomes dominant. At the instant when the second harmonic is dominant the output of the PLL tuned to the second harmonic goes high. The PLLs tuned to the first and third harmonic behave in a like manner. the three branches of monostable circuits generate coincidental positive pulses. In the case of the Humble cite coincidental pulses are generated when the pulse that comes from the second harmonic is delayed most (by t2"), the pulse from the third harmonic is delayed less (by t3") and the pulse from the first harmonic least (by t1"), as shown in FIG. 14. These coincidental pulses are brought to an input of an AND gate 28. Consequently, the output of the AND gate goes high when the pipeline is hit with a hard object. The delays introduced by the monostable circuits are adjustable, in order to accommodate pipelines with different mechanical dimensions which give different transient responses of the first three harmonics.

The propagation of acoustic waves through a pipeline can be described by a complex wave equation in terms of particle displacement from its mean position, the speed of sound c in the pipeline and the Laplace operator. Solving this equation, however, is not easy. Pipeline geometry does not yield simplifications. furthermore, because the pipeline might be buried, possibly in wet ground, the characteristic acoustic impedances of the metal and the ground are relatively close in magnitude, and losses of acoustic power occur at the boundaries. In order to avoid solving the equation, an acoustic transmission line model of the pipeline is utilized. This model is similar to the electric transmission line. The electric elements: R the resistance-per-unit length, L the inductance-per unit length, C the capacitance-per-unit length, and G the leakage conductance-per-unit length are replaced with the appropriate mechanical constants: $R_m$ the damping due to friction-per-unit length, M the mass-per-unit length, $C_m$ the compliance-per-unit length, and $G_m$ the loss at the boundaries-per-unit length, respectively.

Assuming that a force F is acting at one end of the transmission line and the other end of the line is loaded with mechanical impedance $Z_r$, the force $F_m$ at an element dx, at a distance x from the loaded end, a simpler equation is possible. The force, particle velocity and the propagation constant are all phasor quantities and thus are complex and depend on frequency.

Applying a standard sound source at one end of the line, the force anywhere along the line can be measured by a transducer. With a sufficient number of measurements, the new equation becomes a system of equations which can be solved for the unknown transmission line parameters. The sound source was produced by a steel ball, 1 inch in diameter, that was dropped on the pipeline from the height of 4 inches for the invention. This produced a sound impulse in the pipe that was then measured at a number of points along the pipeline. In the model, the length of the transmission line L was set to 500 feet. The system of equations is still difficult to solve, even if sophisticated numerical methods are used. Because the large length of the pipeline and also the ground it is buried in are uniform throughout, $Z_0 = Z_r$, a greatly simplified form is possible:

$$F_m = F_r e^{gx} \tag{9}$$

and taking logarithms of both sides gives:

$$l_m F_m = l_m F_r + gx \tag{10}$$

Which is a linear relation in g or the propagation constant.

While specific embodiments of the invention have been shown and described in detail to illustrate the application of the principles of the invention, it will be understood that the invention may be embodied otherwise without departing from such principles.

What is claimed is:

1. A device for monitoring a pressurized vessel for an occurrence of small leaks or ruptures or hard hits, comprising:
    a plurality of acoustic transducers at spaced sensor locations on the vessel, each responsive to sounds from the vessel at each sensor location, to generate acoustic signals from each sensor location; and
    a central processor connected to each of said transducers and including spectra means for repeatedly recording a frequency spectrum of the acoustic signal from each transducer, the frequency spectrum being selected to contain the dominant resonant frequencies of the vessel, the central processor including program means containing a dominant resonant frequency for the vessel and analysis means for detecting peaks in each spectra at the dominant frequency, the presence of peaks indication the existence of a small leak in the vessel.

2. A device according to claim 1, wherein the central processor comprises a digital computer programmed to form the spectra means and the analysis means.

3. A device according to claim 1, wherein each spectrum contains multiple frequency components, said analysis means including means for detecting a shift of the multiple frequency components to a lower frequency, and a remaining of the multiple frequency components at the lower frequency, which indicates a rupture in the vessel.

4. A device according to claim 1, including means for determining an amplitude of a plurality of harmonics of the acoustic signal and means for detecting a transient response of the harmonics which is an indication of a hard hit on the vessel.

5. A device according to claim 1, wherein the acoustic transducers are each a mechanical transducer containing a resonant gate transistor.

6. A device according to claim 5, wherein each transducer comprises a cantilevered gate electrode connected to an input plate for receiving acoustic signals from the vessel.

7. A device for monitoring a pressurized vessel for an occurrence of a rupture, comprising:
    at least one acoustic transducer on the vessel and responsive to sounds from the vessel to generate acoustic signals; and
    a central processor connected to said transducer and including spectra means for repeatedly recording a frequency spectrum of the acoustic signal, the frequency spectrum being selected to contain the dominant resonant frequencies of the vessel, each spectrum containing multiple frequency components, the central processor including analysis means for detecting a shift of the multiple frequency components to lower frequency and a remaining of the frequency components at the lower frequency, indicating a rupture in the vessel.

8. A device according to claim 7, wherein the acoustic transducer comprises a mechanical transducer containing a resonant gate transistor.

9. A device for monitoring a pressurized vessel for an occurrence of a hard hit, comprising:
    at least one acoustic transducer on the vessel, responsive to sounds from the vessel to generate acoustic signals;
    a central processor connected to said transducer and including means for recording dominant harmonics such as the first, second and third harmonics of the acoustic signal from the transducer, the central processor including analysis means for detecting a transient response of the harmonics which is indicative of a hard hit to the vessel; and
    a plurality of phase locked loops, each tuned to a different harmonic of the acoustic signal, said phase locked loops being connected to the at least one acoustic transducer for receiving the acoustic signal therefrom, a delay circuit connected to each phase locked loop for delaying the acoustic signal by different amounts of time and addition means connected to the delay circuits for adding delayed acoustic signals to each other to detect the transient response.

10. A device according to claim 9, wherein the device includes three phase locked loops, one tuned to the first harmonic, another tuned to the second harmonic and a third tuned to the third harmonic, each of the delay circuits generating a delay pulse having a different duration for detecting the transient response.

11. A device according to claim 9, wherein the acoustic transducer comprises a mechanical transducer containing a resonant gate transistor.

12. A device for monitoring a pressurized vessel for the occurrence of small leaks, ruptures or hard hits comprising:

a cantilevered gate electrode;

an input force plate connected to the vessel and to the cantilevered gate electrode for receiving an acoustic signal from the vessel and transmitting it to the cantilevered gate electrode;

electric signal generating means connected to the gate electrode for generating an electric signal correspondent to the acoustic signal; and processing means connected to the signal generating means for producing a frequency spectrum corresponding to the acoustic signal and at in a range of frequencies containing dominant resonant frequencies of the vessel, the processing means including means for containing a dominant resonant frequency for the vessel and analysis means for detecting peaks in each frequency spectrum at the dominant frequency, the presence of peaks indicating the existence of a small leak in the vessel.

13. A device according to claim 12, wherein the processing means comprises analysis means for detecting a shift of multiple frequency components to lower frequencies in each frequency spectrum, and a remaining of the multiple frequency components at the lower frequency, the shift and remaining of the frequency components at the lower frequency indicating a rupture in the vessel.

14. A device according to claim 12, wherein the processing means includes means for determining an amplitude of a plurality of harmonics of the acoustic signal and means for detecting a transient response of the harmonics which indicates a hard hit on the vessel.

15. A device according to claim 14, wherein said means for determining an amplitude of a plurality of harmonics of the acoustic signal comprise a plurality of phase locked loops, each tuned to a different harmonic of the acoustic signal, each phase locked loop being connected to the signal generating means, the means for detecting a transient response comprising a plurality of delay circuits, each connected to one of the phase locked loops for applying a different dealy to the output of each phase locked loop, and an addition circuit connected to each of the delay circuits for adding the outputs of the delay circuits to each other for detecting the transient response.

* * * * *